United States Patent
Gupta et al.

(10) Patent No.: US 11,550,956 B1
(45) Date of Patent: *Jan. 10, 2023

(54) LINKING OF TOKENIZED TRIAL DATA TO OTHER TOKENIZED DATA

(71) Applicant: Datavant, Inc., San Francisco, CA (US)

(72) Inventors: Serena Gupta, Woodside, CA (US); Samuel A. Roosz, San Francisco, CA (US); Jason A. LaBonte, Natick, MA (US); Vera Mucaj, San Francisco, CA (US); James O'brien, San Francisco, CA (US); Anjali Suresh, Sunnyvale, CA (US)

(73) Assignee: Datavant, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/464,246

(22) Filed: Sep. 1, 2021

Related U.S. Application Data

(63) Continuation of application No. 17/359,051, filed on Jun. 25, 2021.

(60) Provisional application No. 63/085,979, filed on Sep. 30, 2020.

(51) Int. Cl.
  *G06F 21/62* (2013.01)
  *G06F 21/60* (2013.01)
  *G16H 10/20* (2018.01)

(52) U.S. Cl.
  CPC ........ *G06F 21/6254* (2013.01); *G06F 21/602* (2013.01); *G16H 10/20* (2018.01)

(58) Field of Classification Search
  CPC .... G06F 21/6254; G06F 21/602; G16H 10/20
  See application file for complete search history.

(56) References Cited

U.S. PATENT DOCUMENTS

| | | | |
|---|---|---|---|
| 5,892,900 A | 4/1999 | Ginter et al. | |
| 6,397,224 B1 | 5/2002 | Zubeldia et al. | |
| 6,732,113 B1 | 5/2004 | Ober et al. | |
| 6,734,886 B1 | 5/2004 | Hagan et al. | |
| 6,804,787 B2 | 10/2004 | Dick | |
| 7,120,928 B2 | 10/2006 | Sheth et al. | |
| 7,269,578 B2 | 9/2007 | Sweeney | |
| 7,376,677 B2 | 5/2008 | Ober et al. | |
| 7,428,706 B2 | 9/2008 | Hagan et al. | |
| 7,519,591 B2 | 4/2009 | Landi et al. | |

(Continued)

OTHER PUBLICATIONS

Lawson WO-2009/010718-A1 (Year: 2009).*

(Continued)

*Primary Examiner* — Joseph P Hirl
*Assistant Examiner* — Stephen T Gundry
(74) *Attorney, Agent, or Firm* — Morse, Barnes-Brown & Pendleton, P.C.; Sean D. Detweiler, Esq.

(57) ABSTRACT

Systems and methodologies for generating a bridge file linking a subject identifier (Subject ID) (or a tokenized subject identifier), used to anonymize a subject in a trial, to tokenized personal identification information (PII), used to de-identify other data for the subject, without revealing the link between the subject identifier (subject ID) and the personal identifying information (PII) for the subject. The bridge file can then be used to link trial data for the subject anonymized with a subject ID to other data for the subject de-identified with tokenized PII.

30 Claims, 10 Drawing Sheets

(56) References Cited

U.S. PATENT DOCUMENTS

| | | | |
|---|---|---|---|
| 7,526,485 | B2 | 4/2009 | Hagan et al. |
| 7,543,149 | B2 | 6/2009 | Ricciardi et al. |
| 7,587,366 | B2 | 9/2009 | Grim, III et al. |
| 7,668,835 | B2 | 2/2010 | Judd et al. |
| 7,711,120 | B2 | 5/2010 | Kimmel et al. |
| 7,792,517 | B2 | 9/2010 | Mowry et al. |
| 7,827,234 | B2 | 11/2010 | Eisenberger et al. |
| 7,865,376 | B2 | 1/2011 | Ober et al. |
| 7,945,048 | B2 | 5/2011 | Ricciardi et al. |
| 8,024,339 | B2 | 9/2011 | Barker et al. |
| 8,037,052 | B2 | 10/2011 | Kariathungal et al. |
| 8,042,193 | B1 | 10/2011 | Piliouras |
| 8,069,053 | B2 | 11/2011 | Gervais et al. |
| 8,090,595 | B2 | 1/2012 | Hartman |
| 8,121,984 | B2 | 2/2012 | Barbieri et al. |
| 8,176,334 | B2 | 5/2012 | Vainstein |
| 8,275,850 | B2 | 9/2012 | Kohan et al. |
| 8,296,299 | B2 | 10/2012 | Haskell et al. |
| 8,296,341 | B2 | 10/2012 | Hagan et al. |
| 8,341,427 | B2 | 12/2012 | Auradkar et al. |
| 8,355,923 | B2 | 1/2013 | Gervais et al. |
| 8,364,969 | B2 | 1/2013 | King |
| 8,381,287 | B2 | 2/2013 | Trotter |
| 8,473,452 | B1 | 6/2013 | Ober et al. |
| 8,494,874 | B2 | 7/2013 | Green, III et al. |
| 8,560,456 | B2 | 10/2013 | Williams |
| 8,566,113 | B2 | 10/2013 | Friedlander et al. |
| 8,577,933 | B2 | 11/2013 | Evenhaim |
| 8,589,437 | B1 | 11/2013 | Khomenko et al. |
| 8,661,249 | B2 | 2/2014 | Guarraci et al. |
| 8,683,552 | B2 | 3/2014 | Nonaka et al. |
| 9,292,707 | B1 | 3/2016 | Fontecchio |
| 9,614,814 | B2 | 4/2017 | Fontecchio |
| 9,734,169 | B2 | 8/2017 | Redlich et al. |
| 9,830,476 | B2 | 11/2017 | Fontecchio |
| 9,928,379 | B1 * | 3/2018 | Hoffer .................... G16H 50/20 |
| 9,977,775 | B2 | 5/2018 | Cougias et al. |
| 10,129,370 | B2 | 11/2018 | Levy et al. |
| 10,200,397 | B2 | 2/2019 | Dhar et al. |
| 10,255,456 | B2 | 4/2019 | Guglani et al. |
| 10,305,911 | B1 | 5/2019 | Eyre et al. |
| 10,713,390 | B2 | 7/2020 | Anderson et al. |
| 10,789,324 | B2 * | 9/2020 | Longo .................... G06F 16/957 |
| 10,891,610 | B2 * | 1/2021 | Powell .................... G06Q 20/40 |
| 10,902,081 | B1 * | 1/2021 | Gassner ................ G06F 16/957 |
| 10,984,128 | B1 * | 4/2021 | Hoffer .................... G16B 50/00 |
| 11,004,548 | B1 * | 5/2021 | Austin ................... H04L 9/3226 |
| 11,042,668 | B1 * | 6/2021 | Kassam-Adams .... G06F 21/572 |
| 11,080,240 | B2 * | 8/2021 | Madisetti ............... G06F 16/176 |
| 11,080,423 | B1 * | 8/2021 | Kassam-Adams ..... G16H 15/00 |
| 11,081,219 | B1 * | 8/2021 | Dods ..................... G06N 3/0454 |
| 11,120,144 | B1 * | 9/2021 | Kassam-Adams .......................... G06F 21/6245 |
| 11,222,139 | B2 * | 1/2022 | Jones .................... G06F 16/901 |
| 11,245,691 | B1 * | 2/2022 | Dods ....................... G06N 20/00 |
| 2002/0073138 | A1 | 6/2002 | Gilbert et al. |
| 2002/0173971 | A1 | 11/2002 | Stirpe et al. |
| 2006/0053032 | A1 | 3/2006 | Weiler et al. |
| 2007/0162377 | A1 | 7/2007 | Williams |
| 2007/0255704 | A1 | 11/2007 | Baek et al. |
| 2008/0147554 | A1 | 6/2008 | Stevens et al. |
| 2009/0106550 | A1 | 4/2009 | Mohamed |
| 2009/0287502 | A1 | 11/2009 | Roberts et al. |
| 2010/0042583 | A1 | 2/2010 | Gervais et al. |
| 2010/0070306 | A1 | 3/2010 | Dvorak et al. |
| 2010/0094758 | A1 | 4/2010 | Chamberlain et al. |
| 2010/0114607 | A1 | 5/2010 | Kress et al. |
| 2010/0205009 | A1 | 8/2010 | Kostoff |
| 2010/0211781 | A1 | 8/2010 | Auradkar et al. |
| 2010/0223467 | A1 | 9/2010 | Dismore et al. |
| 2010/0256994 | A1 | 10/2010 | Eisenberger et al. |
| 2011/0191245 | A1 | 8/2011 | Ricciardi et al. |
| 2012/0036360 | A1 | 2/2012 | Bassu et al. |
| 2012/0116800 | A1 | 5/2012 | McCallie et al. |
| 2012/0124637 | A1 | 5/2012 | Dunaway |
| 2012/0159637 | A1 | 6/2012 | Dove et al. |
| 2012/0204032 | A1 | 8/2012 | Wilkins et al. |
| 2012/0226916 | A1 | 9/2012 | Hahn et al. |
| 2012/0303558 | A1 | 11/2012 | Jaiswal |
| 2012/0316898 | A1 | 12/2012 | Levitt et al. |
| 2013/0117126 | A1 | 5/2013 | Coppinger |
| 2013/0117128 | A1 | 5/2013 | Coppinger |
| 2013/0167192 | A1 | 6/2013 | Hickman et al. |
| 2013/0246097 | A1 | 9/2013 | Kenney et al. |
| 2013/0304504 | A1 | 11/2013 | Powell |
| 2013/0304542 | A1 | 11/2013 | Powell |
| 2013/0346104 | A1 | 12/2013 | Pillai |
| 2014/0013452 | A1 | 1/2014 | Aissi et al. |
| 2014/0040308 | A1 | 2/2014 | Ober et al. |
| 2014/0041047 | A1 | 2/2014 | Jaye et al. |
| 2014/0108049 | A1 | 4/2014 | Fuhrmann et al. |
| 2014/0108258 | A1 | 4/2014 | Williams |
| 2014/0122873 | A1 | 5/2014 | Deutsch et al. |
| 2015/0089357 | A1 | 3/2015 | Vandervort et al. |
| 2015/0095243 | A1 | 4/2015 | Eller et al. |
| 2015/0095252 | A1 | 4/2015 | Mattsson et al. |
| 2015/0149208 | A1 | 5/2015 | Lynch et al. |
| 2016/0110648 | A1 | 4/2016 | Baveja et al. |
| 2016/0147945 | A1 | 5/2016 | MacCarthy et al. |
| 2016/0267238 | A1 | 9/2016 | Nag |
| 2016/0275309 | A1 | 9/2016 | Austin et al. |
| 2016/0344544 | A1 | 11/2016 | Biesinger et al. |
| 2017/0103179 | A1 | 4/2017 | Jiao et al. |
| 2017/0243028 | A1 | 8/2017 | LaFever et al. |
| 2020/0162255 | A1 * | 5/2020 | Hunt ..................... H04L 63/083 |
| 2020/0265516 | A1 * | 8/2020 | Xu ........................ G06Q 40/04 |
| 2020/0285770 | A1 * | 9/2020 | Brannon ............. G06F 21/6245 |
| 2020/0358614 | A1 * | 11/2020 | Fiske .................... H04L 9/3252 |
| 2020/0364369 | A1 * | 11/2020 | Brannon ................. G06F 21/33 |
| 2020/0381087 | A1 * | 12/2020 | Ozeran ................. G16H 10/60 |
| 2020/0402625 | A1 * | 12/2020 | Aravamudan .......... G06F 21/64 |
| 2021/0012332 | A1 * | 1/2021 | Ow ..................... G06Q 20/3678 |
| 2021/0065267 | A1 * | 3/2021 | Smith ................ G06Q 20/4014 |
| 2021/0081366 | A1 * | 3/2021 | Madisetti ............... G06F 16/176 |
| 2021/0182423 | A1 * | 6/2021 | Padmanabhan ..... G06F 21/6245 |
| 2021/0209249 | A1 * | 7/2021 | Hoffer ................. G06F 21/6245 |
| 2021/0248268 | A1 * | 8/2021 | Ardhanari ............. G06F 21/602 |
| 2021/0256070 | A1 * | 8/2021 | Tran ................. G06F 16/90332 |
| 2021/0263971 | A1 * | 8/2021 | Landes ................. G06F 16/313 |
| 2021/0319436 | A1 * | 10/2021 | Ow ....................... G06Q 20/367 |
| 2021/0350891 | A1 * | 11/2021 | Dods ....................... G06F 17/18 |
| 2022/0050921 | A1 * | 2/2022 | LaFever ................ G16H 10/60 |
| 2022/0172809 | A9 | 6/2022 | Lyman et al. |

OTHER PUBLICATIONS http://mist-deid.sourceforge.net/ "MIST—The MITRE Identification Scrubber Toolkit".

Third Party Submission Under 37 CFR 1.290 from U.S. Appl. No. 15/045,605, made/submitted Mar. 29, 2019.

Non-Final Office Action from U.S. Appl. No. 15/045,605, dated Jul. 18, 2019.

Final Office Action from U.S. Appl. No. 15/045,605, dated Nov. 4, 2019.

Non-Final Office Action from U.S. Appl. No. 15/045,605, dated Feb. 13, 2020.

Final Office Action from U.S. Appl. No. 15/045,605, dated May 8, 2020.

Non-Final Office Action from U.S. Appl. No. 16/135,972, dated Aug. 13, 2020.

Notice of Allowance for U.S. Appl. No. 15/045,605, dated Oct. 14, 2020.

Non-Final Office Action from U.S. Appl. No. 16/382,462, dated Oct. 29, 2020.

Non-Final Office Action from U.S, U.S. Appl. No. 16/382,447, dated Dec. 16, 2020.

Notice of Allowance from U.S. Appl. No. 16/135,972, dated Jan. 28, 2021.

Non-Final Office Action from U.S. Appl. No. 16/684,541, dated Feb. 18, 2021.

Notice of Allowance from U.S. Appl. No. 16/382,462, dated Mar. 3, 2021.

(56) References Cited

OTHER PUBLICATIONS

Notice of Allowance from U.S. Appl. No. 16/382,447, dated Apr. 12, 2021.
Non-Final Office Action from U.S. Appl. No. 16/255, 443, dated Mar. 22, 2022.
Notice of Allowance from U.S. Appl. No. 16/382,428, dated May 27, 2021.
Notice of Allowance from U.S. Appl. No. 16/684,541, dated Jun. 8, 2021.
Notice of Allowance from U.S. Appl. No. 16/255,443, dated Sep. 12, 2022.

* cited by examiner

LINKING OF TOKENIZED TRIAL DATA TO OTHER TOKENIZED DATA

CROSS-REFERENCE TO RELATED APPLICATION(S)

This application is a continuation of and claims the benefit of and priority to co-pending U.S. patent application Ser. No. 17/359,051 filed Jun. 25, 2021, which claims priority to and the benefit of U.S. Provisional Application 63/085,979, filed Sep. 30, 2020, for all subject matter in said applications. The disclosures of said application are hereby incorporated by reference in their entirety.

FIELD OF THE INVENTION

The present invention relates generally to a method and system for linking data for a subject in a trial, where the subject is identified by a subject identifier (Subject ID) rather than personal identifying information, which in some cases has been further de-identified using tokenizing and other techniques, with other data for the subject, where the subject is identified by personal identifying information (PII), and that has also been de-identified using tokenizing and other techniques. More specifically, the present invention relates to a method and system that generates a link between an identification of the subject in the trial (subject ID) (or a subject identification token), used to de-identify the trial data for the subject, and personal identification information tokens, used to de-identify other data for the subject so that trial data can be linked to tokenized other data for the subject without violating the privacy of the subject and without unblinding the trial.

BACKGROUND

Generally, regulations and laws protecting the privacy of personal data have created a plethora of strategies for protecting the identity of personal data. For example, it is a potential Health Insurance Portability and Accountability Act (HIPAA) violation to incorporate personal health information (PHI) elements into a healthcare data set. Accordingly, to be compliant with government regulations, all PHI data elements must be removed and/or de-identified before being incorporated into any healthcare data set. Typically, institutions, organizations, and businesses that create personal data have their own methods for complying with identity protection laws. These methods may include in-house developed proprietary methods, or one of many disparate off-the-shelf solutions. The conventional methods utilized for protecting personal data have been responsible for serious identity breaches resulting in the theft of customer and employee personal information. Conventional methods implement processes of de-identification by the use of hashing methods applied to strings of characters generated from private data elements in data records. These conventional processes are built using a single hashing seed or encryption key, which is shared across many disparate target sites. Such systems suffer the risk that the resulting generated values can be mapped back to the original source data. Once a breach has occurred, all the target data sites have exposed values which, in themselves, could become regulated data values. Conventional processes also create problems because once PHI data elements are removed from record, users have no way to understand which individuals in the data set match the de-identified individuals, and so conventional healthcare data systems are limited in their ability to identify the existence of duplicate records or duplicate individuals from individual de-identified records in healthcare data sets.

Additionally, the personal data records stored by the various entities cannot be shared or aggregated for any meaningful or useful data analysis. Specifically, the personal data cannot be shared between entities where the identity any one particular individual is of no importance. A problem associated with protected personal data is easily recognizable in the industries related to healthcare where each provider or insurer typically employs their own proprietary methods for de-identifying personal data records, making it nearly impossible to do any meaningful aggregations of the data for important clinical research or cost analysis at higher regional, state, or national levels. This problem is compounded by the fact that there are many separate and distinct companies involved with the care of an individual patient, making it difficult to share and or tie the information together for a single patient once the stake holder has applied their own proprietary de-identification process to the patient's personal data records.

Standardized solutions, such as Datavant's de-dentification and linking solutions have been developed to address these issues. However, even with a standardized way of de-identifying and linking data based on tokenizing the personal identifying information (PII) of the individual associated with the data, trials, such as clinical trials, provide additional issues. Typically, each participant in a trial is identified with a subject identifier (Subject ID) rather than their personal identifying information (PII) to maintain anonymity. For example, the subject named "John Smith" might be identified as "Subject 12" for the purposes of the data collected and presented in the trial. This additional layer of abstraction means that data for a subject from the trial cannot be easily linked to other data for the subject that has been de-identified in conventional manner by tokenizing the personal identification information (PII) associated with the data. Since the subject in the trial is identified by a subject ID, there is no personal identification information (PII) associated with the trial data to be encrypted and linked to other data using such standardized solutions. While the trial site might collect the subject's PII when setting up the trial, the PII never leaves the trial site. The trial originator or sponsor or other entities interested in the data only get the subject ID identification associated with the trial data.

SUMMARY

Thus, there is a need for a solution that can link data from a trial, where the subject is anonymized with a subject identifier (Subject ID), to other data that has been de-identified by tokenizing the personal identifying information (PII) for the individual associated with the data while maintaining the privacy of the subject. The present invention is directed toward further solutions to address this need, in addition to having other desirable characteristics. Specifically, the present invention creates a link between a subject identifier (or a tokenized subject identifier) for the subject in the trial and the tokenized personal identification information of the subject without revealing the link between the subject identifier and the personal identification information.

In accordance with example embodiments of the present invention, a method of linking trial data for a subject with other tokenized data for the subject is provided. The method involves receiving an identification of a subject in the trial (subject ID); receiving personal identification information (PII) for the subject; generating multiple tokens from personal identification information (PII) for the subject; generating a bridge file mapping a link between the identification of the subject (subject ID) and the multiple personal identification information tokens; and sending the bridge file to a storage location.

These steps of the method are performed by trial token generation software on a first client site. The resulting multiple personal identification information tokens are unique to the first client site and the subject. The bridge file links trial data for the subject to other data for the subject tokenized with the multiple personal identification information tokens. Only the first client site has access to the subject identification (subject ID), personal identification information (PII), and the link between the subject identification and personal identification information for the subject.

In accordance with an aspect of the present invention, the trial token generation software is downloaded from a central management platform (vault).

In accordance with an aspect of the present invention, the method further includes registering, by a trial originator/sponsor, the trial with a central management platform (vault).

In accordance with an aspect of the present invention, the method further includes registering the first client site with a central management platform. The central management platform assigns a unique encryption key to the first client site. The unique encryption key used by the trial token generation software to generate the multiple personal identification information tokens.

In accordance with an aspect of the present invention, multiple subjects participate in the trial and an identification the subject in the trial (subject ID) and personal identification information (PII) is provided for each of the multiple participants and multiple personal identification tokens are generated for each of the multiple participants in the trial. The generated bridge file links the identification of the subject in the trial (subject ID) and multiple personal identification tokens for each participant in the trial.

In accordance with an aspect of the present invention, the storage location is located at a trial originator/sponsor.

In accordance with an aspect of the present invention, the method further includes assigning, at the first client site, an identification for a subject (subject ID) in the trial; and collecting, at the first client site, personal identification information (PII) for the subject in the trial.

In accordance with an aspect of the present invention, the method further includes obtaining, at the first client site, the subject's consent for participation in the trial.

In accordance with an aspect of the present invention, generating a multiple personal identification tokens and generating a bridge file, are performed as a batch process where the personal identification information is sent to a secure location where an application at the secure location generates the multiple personal identification tokens and returns the personal identification tokens to the trial token generation software.

In accordance with an aspect of the present invention, the method further includes tokenizing other data for the subject, and linking the trial data with the tokenized other data. The tokenizing is performed using de-identification software. The linking is performed using linking software. In certain such aspects, tokenizing other data is performed at the trial originator/sponsor. The linking software may be downloaded from a central management platform (vault).

In some such aspects, tokenizing other data for the subject involves generating one or more personal identification information tokens from the personal identification information of the subject and replacing the personal identification information (PII) associated with the trial data with one or more personal identification information tokens. In certain such aspects, tokenizing other data is performed at a second client site. In some such aspects, the second client is registered with central management platform (vault). The central management platform assigns a unique encryption key to the second client site. The unique encryption key used by the de-identification software to generate the one or more personal identification information tokens. The de-identification software may be downloaded from a central management platform (vault).

In some such aspects, linking the trial data for the subject to the tokenized other data for the subject involves replacing the one or more identification information tokens associated with the other data with one or more shared encryption format person identification information tokens; replacing the one or more personal identification information tokens in the bridge file with one or more shared encryption format personal identification information tokens; and linking the trial data of the subject to the other data for the subject based on the shared encryption format tokens.

In accordance with an aspect of the invention, the method further includes generating, using trial token generation software at a first client site, a subject identification token from an identification of subject in the trial (subject ID). The subject identification token is unique to the first client site and the trial. The generated bridge file maps a link between the subject identification token and the multiple personal identification information tokens. The bridge file links trial data for the subject tokenized with the subject identification token to other data for the subject tokenized with the multiple personal identification information tokens.

In some such aspects, this further includes registering the first client site with a central management platform wherein the central management platform assigns a unique encryption key to the first client site. The unique encryption key used by the trial token generation software to generate the subject identification token and the multiple personal identification information tokens.

In some such aspects, wherein multiple subjects participate in the trial, a subject identification token and multiple personal identification tokens are generated for each of the multiple participants in the trial, and the bridge file links the subject identification token and multiple personal identification tokens for each participant in the trial.

In some such aspects, generating a subject identification token, generating a multiple personal identification tokens, and generating a bridge file, are performed as a batch process where the subject identification and personal identification information is sent to a secure location where an application at the secure location generates the subject identification token and the multiple personal identification token and returns the subject identification token and the personal identification token to the trial token generation software.

In some such aspects, the method further includes tokenizing, with de-identification software, trial data using a subject identification token; tokenizing, with de-identification software, other data for the subject using one or more personal identification information tokens; and linking, with linking software, the tokenized trial data for the subject to the tokenized other data for the subject using the bridge file.

In certain such aspects tokenizing trial data includes generating a subject identification token from the identification of the subject in the trial (subject ID) and replacing the identification of the subject (subject ID) associated with the trial data with a subject identification token. In certain such aspects, tokenizing trial data, with de-identification software, is performed at the trial originator/sponsor. The trial originator or sponsor is registered with the central management platform (vault). The central management platform assigns a unique encryption key to the trial originator or sponsor. The unique encryption key used by the de-identification software to generate the subject identification token. In some such aspects, the de-identification software is downloaded from a central management platform (vault).

In certain such aspects, tokenizing other data for the subject includes generating one or more personal identification information tokens from the personal identification information of the subject; and replacing the personal identification information (PII) associated with the trial data with one or more personal identification information tokens. In some such aspects, the linking software is downloaded from a central management platform (vault). In certain aspects, linking the tokenized trial data for the subject to the tokenized other data for the subject is performed at a trial originator/sponsor.

In certain such aspects, linking the tokenized trial data for the subject to the tokenized other data for the subject includes replacing the subject identification token associated with the trial data with a shared encryption format subject identification token; replacing the one or more identification information tokens associated with the other data with one or more share encryption format personal identification information tokens; replacing the subject identification token linked to the one or more personal identification information tokens in the bridge file with a shared encryption format subject identification token linked to one or more shared encryption format personal identification information tokens; and linking the trial data of the subject to the other data for the subject based on the shared encryption format tokens.

In accordance with example embodiments of the present invention a method of linking tokenized trial data for a subject with other tokenized data for the subject is provided. The method involves generating a subject identification token from an identification of subject in the trial (subject ID), generating multiple tokens from personal identification information (PII) for the subject, generating a bridge file mapping a link between the subject identification token and the multiple personal identification information tokens, and sending the bridge file from the first client site to a storage location.

These steps of the method are performed by trial token generation software on a first client site. The resulting subject identification token and multiple personal identification information tokens are unique to the first client site and the subject. The bridge file links tokenized trial data for the subject to other data for the subject tokenized with the multiple personal identification information tokens. Only the first client site has access to the subject identification (subject ID), personal identification information (PII), and the link between the subject identification and personal identification information for the subject.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
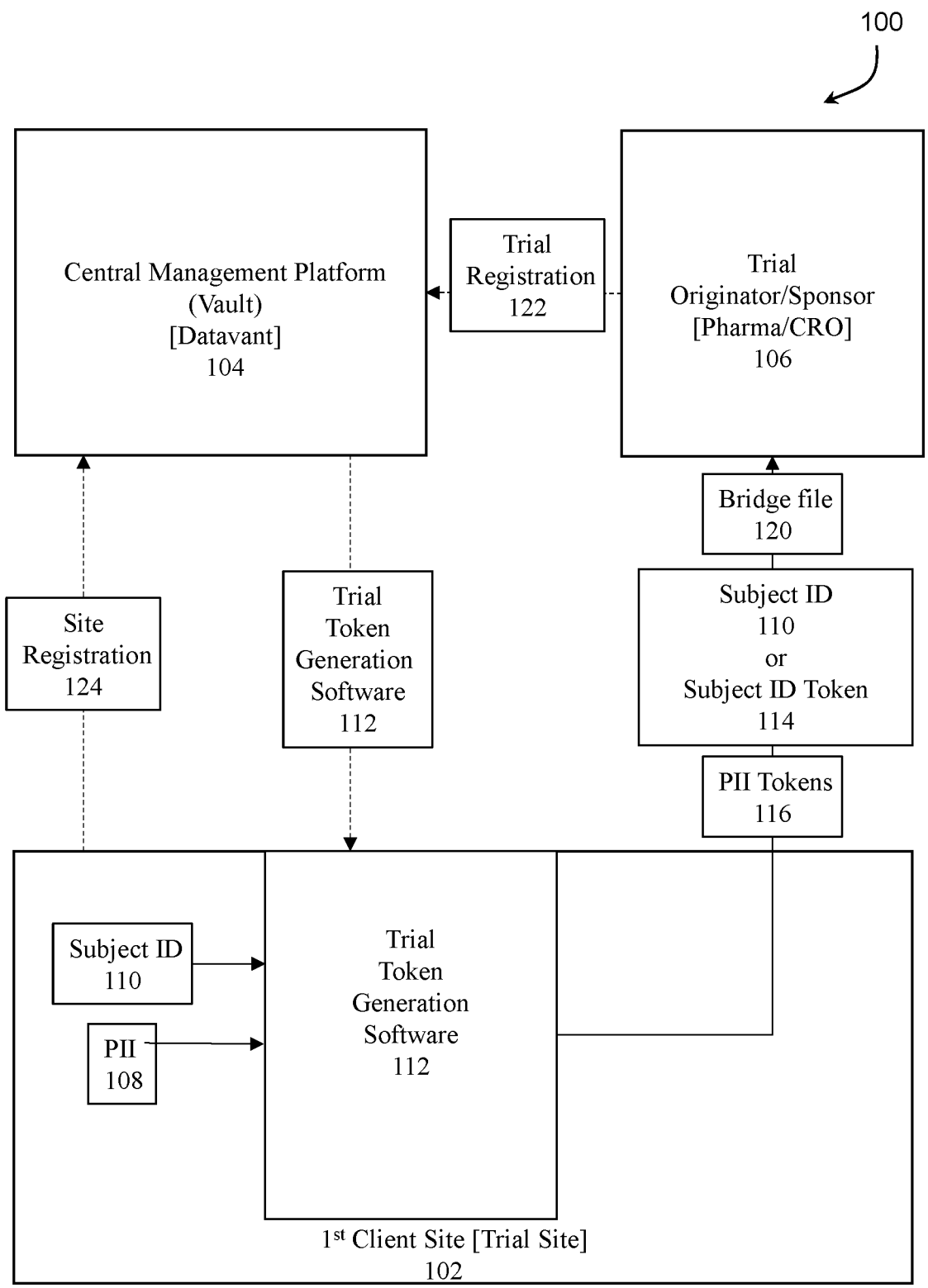
FIG. 1 is a diagrammatic illustration of a system for creating a bridge file linking trial data for a subject with other tokenized data for the subject.
Figure 2:
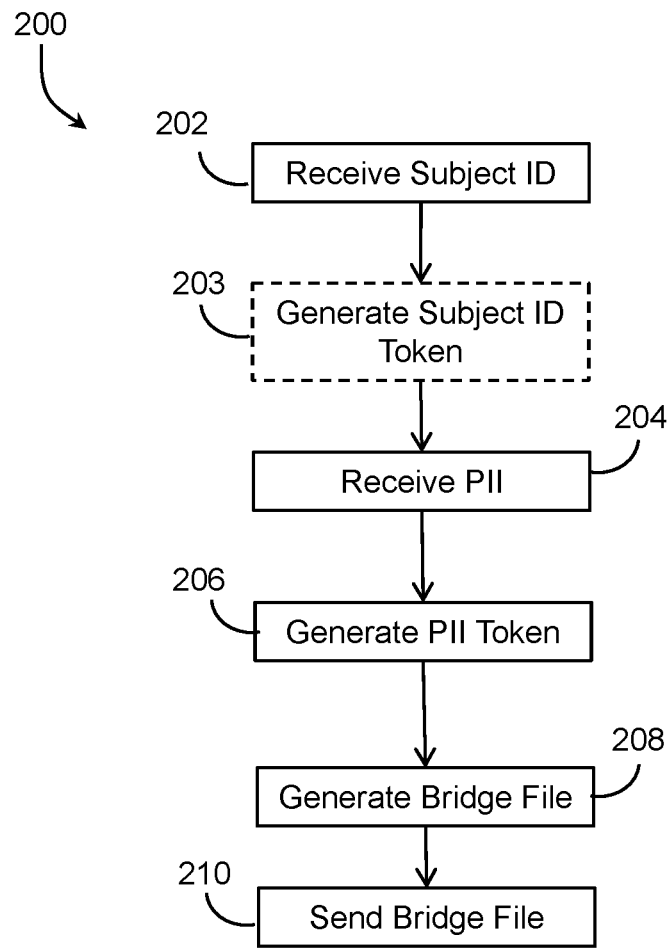
FIG. 2 is an illustrative flow diagram depicting a process performed by a client site during operation.

An illustrative embodiment of the present invention relates to systems and methodologies that create a persistent, anonymized link between data collected on a subject in a trial setting and that subject's data collected in other external systems such as Electronic Health Records and insurance claims (often collectively referred to as "real world data") for the purpose of better understanding effects of the drug or treatment on different types of patients. A bridge is generated. The bridge file links a subject identifier (Subject ID), used to anonymize a subject in a trial, to tokenized personal identification information (PII), used to de-identify other data for the subject, without revealing the link between the subject identifier (subject ID) and the personal identifying information (PII). The bridge file can then be used to link trial data for the subject anonymized with a subject ID to other data for the subject de-identified with tokenized PII. Once the data for the subject is linked or otherwise merged, a user can perform analysis of anonymous healthcare or personal data with the added benefit of the indications for the de-identified individuals originally associated with the records. This functionality provides many added benefits not previously available. The de-identification of healthcare or personal data sets provided by the present invention enables tokens to be merge-able with data sets in such a way that data sets from disparate sources but relating to a same individual can be matched up and associated with each other without the exposure of PII.

FIGS. 1 through 10 wherein like parts are designated by like reference numerals throughout, illustrate an example embodiment or embodiments of systems and methods for linking de-identified trial data of a subject with de-identified other or real-world data for the subject using a bridge file, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed in a manner still in keeping with the spirit and scope of the present invention.

As used herein, the term "trial" refers to any research study that is ongoing, future, or completed including, but not limited to: prospective or retrospective, interventional or observational, registries, etc. Other possible trials will be apparent to one skilled in the art given the benefit of this disclosure.

FIG. 1 depicts a high-level system for the generation of a bridge file used to link trial data for a subject with other or real-world data for the subject. The entities involved in the system 100 of FIG. 1 include a client site 102, a central management platform 104, and a trial originator or sponsor 106.

The client site 102 is typically a site where the trial is run and data for the trial is collected. In certain embodiments, there are multiple client sites 102 set up to collect data for the trial. It is at the client site 102 where the data for the subject is collected. This data includes the personal identification information (PII) 112 for the subject as well as, in some cases, consent from the subject to use the data collected. The client site 102 is also where a subject identifier 110, used to anonymously identify the subject in the trial, is assigned.

The central management platform (or vault) 104 maintains and provides encryption keys for tokenizing used to de-identify data. In certain embodiments, the generates and maintains a unique encryption key, called a salt, as well tokenizing or other encryption rules for every entity (client site 102 or trial sponsor 106) registered with the central management platform 104. In some embodiments, the central management platform 104 also provides software to the entities for the tokenizing of data, de-identifying data, and linking of de-identified data. In the example of FIG. 1, the central management platform 104 also serves to register trials 122 from trial sponsors 106 and the register 124 client sites 102 participating in the trials.

The trial originator or sponsor 106, in accordance with example embodiments, is the company or Clinical Research Organization (CRO) for which the trial is being conducted. The trial originator or sponsor 106 is the entity receiving and analyzing the data collected from the trial. As such, it is typically, the trial originator or sponsor 106 that is interested in linking or otherwise merging the data for a subject from the trial with other data, also called real world data, for the subject. In certain embodiments, the trial or sponsor 106 is the same entity as the client site 102. In other embodiments, the trial originator or sponsor 106 may also include entities authorized to link or otherwise merge data for the subject from the trial with other real world data. In still other embodiments, there may be multiple trial originators or sponsors 106). Other possible entities will be apparent to one skilled in the art given the benefit of this disclosure.

Facilitating linking trial data with other data is the bridge file 120. To generate the bridge file 120, trial token generation software 112 is executed on the client site 102. The trial token generation software 112 performs the process 200 set forth in FIG. 2. An identification of the subject in the trial (subject ID) 110 is received by the trial token generation software 112 running on the client site 102 (Step 202). Personal identification information for the subject (PII) 108 is also received by the trial token software 112 (Step 204). The trial token generation software 112 generates one or more personal identification information tokens 116 from the personal identification information (PII) for the subject (Step 206). The one or more personal identification information tokens 116 are unique to the client site and the subject. The bridge file 120 is then generated (Step 208). The bridge file 120 maps a link between the subject identification (subject ID) 110 and the personal identification information tokens 116. The bridge file 120 is then sent to a storage location (step 210). In certain embodiments, the storage location is at the trial originator or sponsor 106. In other embodiments, the storage location is a designated remote storage location such a server or cloud storage. While the trial originator or sponsor 106 may have access to the bridge file, only the client site 102 that collected the subject's data has access to the subject identifier (subject ID) 110, personal identification information (PII) 108, and the link between the PII 108 and subject ID 110.

In certain embodiments, the trial token generation software 112 running on the client site 102 also generates a subject identification token 114 from the subject identifier (subject ID) 110 for the subject (Step 203). The subject identification token 114 is unique to the client site and the particular trial. In such cases the bridge file 120 maps a link between the subject identification token 114 and the personal identification information tokens 116.

In the embodiment of FIG. 1, the trial token software 112 is downloaded to the client site 102 from the central management platform 104. In other embodiments, the trial originator or sponsor 106 may provide the trial token software 112 to the client site 102. In still other embodiments, the trial token generation software 112 is part of other software operating on the client site 102. In some embodiments, the trial token generation software 112 includes a unique encryption key, sometimes called a salt, as well as the necessary configuration for generating the tokens. In other embodiments, the trial token generation software 112 contacts the central management platform 104 to obtain the unique encryption key and configurations. In certain embodiments, generating multiple personal identification tokens 116 and generating a bridge file 120, (and in some instances, generating a subject identification token 114) are performed as a batch process where the subject identification and personal identification information is sent to a secure location (or central management platform 104) where an application at the secure location generates the multiple personal identification tokens 116 (and in some instances, the subject identification token 114) and returns the personal identification tokens 116 (and possibly the subject identification token 114) to the trial token generation software 112. The encryption key provided is unique to the client site 102 and the trial. Thus, the tokens generated using the unique encryption key are unique to the client site 102, trial, and user. Other deployments or configurations will be apparent to one skilled in the art given the benefit of this disclosure.

While the previous example dealt with a single subject in the trial, it should be understood that there are typically many subjects participating in a trial. In such cases, each subject has PII 108, a subject ID 110, and has personal identification information tokens 116 (and in some instances, a subject identification token 114) generated where the tokens are unique to the client site 102, trial, and subject. The bridge file 120 can include mapping of the link between the subject identification (subject ID 110) (or subject identification token 114) and personal identification information tokens 116 for each subject participating in the trial. Multiple client sites 102, each of which can have multiple subjects, can participate in a trial. Each client site 102 can also participate in multiple trials.

Figure 3:
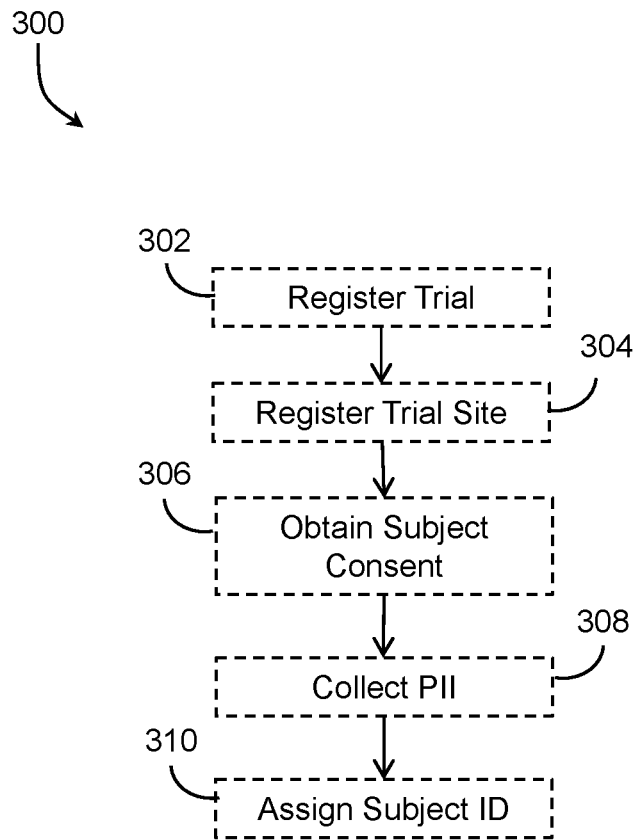
FIG. 3 is an illustrative flow diagram depicting additional steps that may be performed during operation.

FIG. 3 depicts a collection 300 of additional steps that may optionally be performed by the entities of the system of FIG. 1. This collection of steps 300 include the registering of the trial 122 with the central management platform 104 by the trial originator or sponsor 106 (step 302). The collection of steps 300 also include registering 124 the client site 102 as a trial site with the central management platform 104

(Step 304). In some embodiments, the registration of the client site 102 is performed by the trial originator or sponsor 106 as part of the trial registration 122. In other embodiments, the central management platform 104 provides a registration portal to register client sites 102 as trial sites. The collection of steps 300 can also optionally include obtaining subject consent to collect data about the subject and use the collected data (Step 306). This can be performed by the trial token generation software 112 or software running on the client site. In other embodiments, a client consent portal is provided by the central management platform 104 or trial originator or sponsor 106 to obtain subject consent. The collection of steps 300 can also include collecting personal identification information (PII) for the subject(s) in the trial (Step 308) and assigning a subject identification (Subject ID) to the subject(s) in the trial (Step 310). Both or either of these steps can be performed by the trial token generation software 112 or other software running on the client site 102.

With the bridge file generated, data from the trial, which uses the subject identifier (subject ID), can then be linked or otherwise merged with other data ("real world data") for the subject that has been de-identified using tokenizing. An example system for performing this can be seen in FIG. 4. The entities involved in the system 400 of FIG. 4 include a central management platform 104, the trial originator or sponsor 106, and a second client site 402.

The central management platform 104 and trial originator or sponsor 106 are the same entities from FIG. 1. The second client site 402 is typically a site where the other data for a subject is collected. In some embodiments, the registration 420 of a second client site 402 is performed by the central management platform 104, for example, by a registration portal. In other embodiments, the second client site 402 is registered by trial originator or sponsor 106. In certain embodiments, there are multiple second client sites 402 set up to collect data for the subject(s). This data includes the personal identification information (PII) 112 for the subject as well as, in some cases, consent from the subject to use the data collected.

In order to share and eventually link and/or merge the data collected, the data needs to be de-identified in order to comply with various privacy concerns, such as the Health Insurance Portability and Accountability Act (HIPAA). As part of de-identification, the entities handling data (trial originator or sponsor 106 and second client site 402) can make use of de-identifying software 404. The de-identified data can then be linked and otherwise merged using linking software 406 in conjunction with the bridge file 120. The process 500 performed by this software 404, 406 running on these entities 106, 402 can be seen in FIG. 5.

An instance of the de-identifying software 404 is run at the trial originator or sponsor 106 as part of the data intake or preparation 408. Here trial data with a Subject ID 410 provided by a client site 102 collecting trial data is tokenized by the de-identifying software 404 using a subject identification token (step 502). If the trial data 410 is not being tokenized, trial data 410 need not be passed through the de-identifying software 404 at the trial originator or sponsor 106. Another instance of the de-identifying software 404 is run at the second client site 402. Here other data (or "real world data") collected with personal identification information (PII) is tokenized by the de-identifying software 404 using one or more personal identification tokens (step 504). Linking software 406 is run at the location or entity that is interested in linking or merging the data. In this example, the linking software 406 is run at the trial originator or sponsor 106 as part of data linking 40. The un-tokenized trial data 410 or tokenized trial data 412 and tokenized other data 416 can then be linked with the linking software 406 using the bridge file 120 (Step 506).

Figure 4:
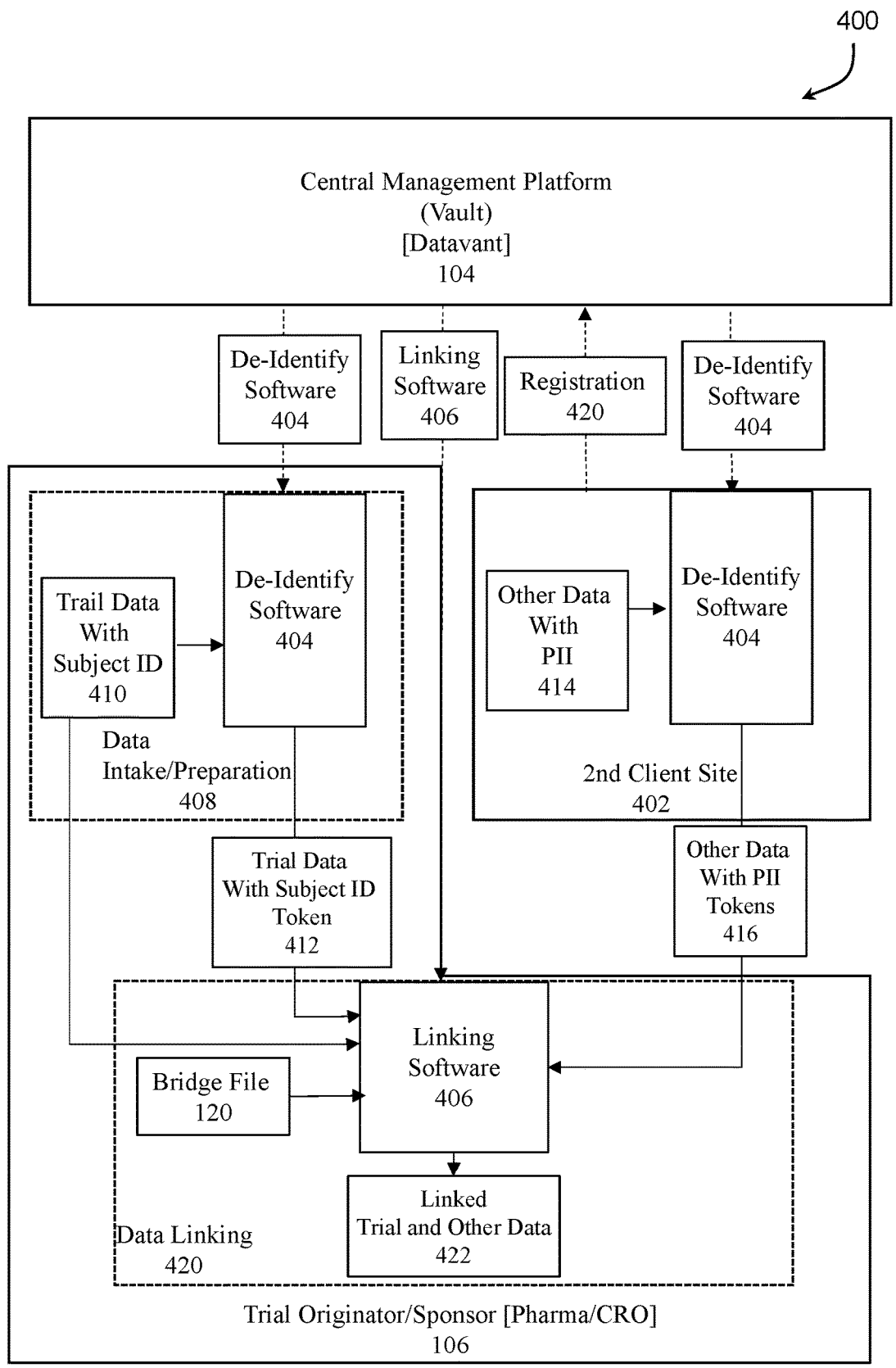
FIG. 4 is another diagrammatic illustration of a system for implementing linking trial data for a subject with other tokenized data for the subject using the bridge file.
Figure 5:
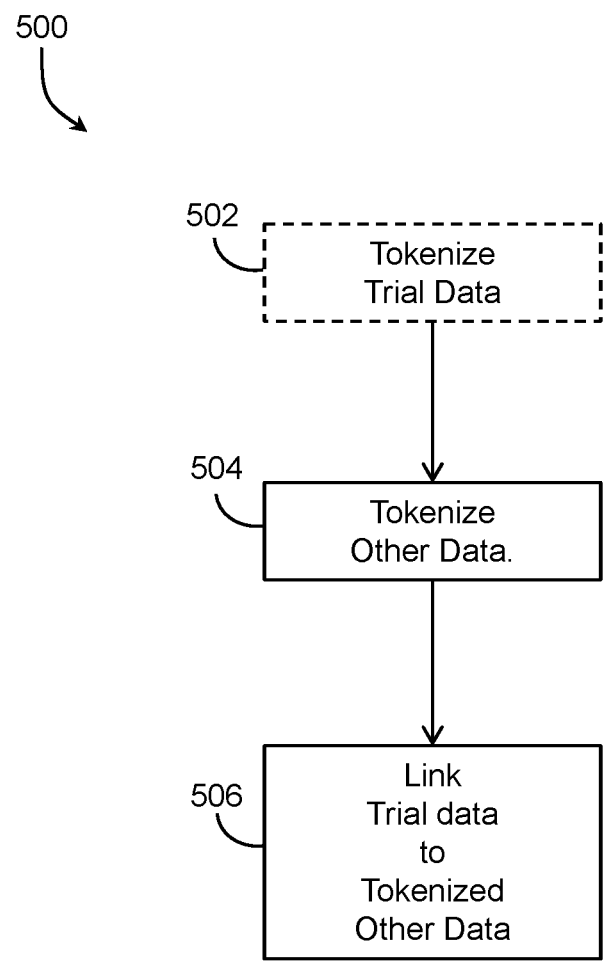
FIG. 5 is an illustrative flow diagram depicting a process performed by the system of FIG. 4 during operation.
Figure 6:
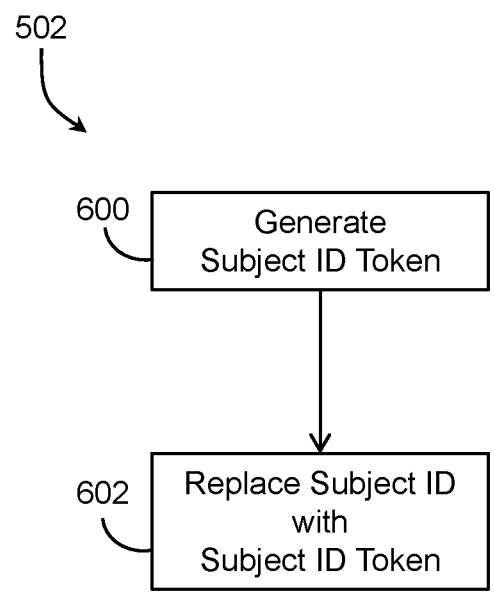
FIG. 6 is an illustrative flow diagram depicting a process performed to tokenize trial data.

FIG. 6 depicts exemplary steps performed if the trial data is being tokenized (Step 502). First, a subject identification token is generated from the subject identification (Subject ID) associated with the trial data (Step 600). Then the subject identification (Subject ID) associated with the trial data is replaced with the generated subject identification token (Step 602). The generation of the subject identification token is performed by tokenizing or otherwise encrypting the subject identifier using a unique encryption key. In the embodiment of FIG. 4, the first instance of the de-identifying software 404 is downloaded to the trial originator or sponsor 106 from the central management platform 104. In some embodiments, the de-identifying software 404 is part of other software operating on the trial originator or sponsor 106. In some embodiments, the de-identifying software 404 includes a unique encryption key, sometimes called a salt, as well as the necessary configuration for generating the tokens. In other embodiments, the de-identifying software 404 contacts the central management platform 104 to obtain the unique encryption key and configurations. The encryption key provided is unique to the trial originator or sponsor 106 and the trial. Thus, the tokens generated using the unique encryption key are unique to the trial originator or sponsor 106 and the trial. In some embodiments, de-identifying the trial data also includes formatting or otherwise configuring the data in addition to the tokenizing. It should also be understood that the tokenizing of the trial data can be performed by or on any of the other entities. Other deployments or configurations will be apparent to one skilled in the art given the benefit of this disclosure.

Figure 7:
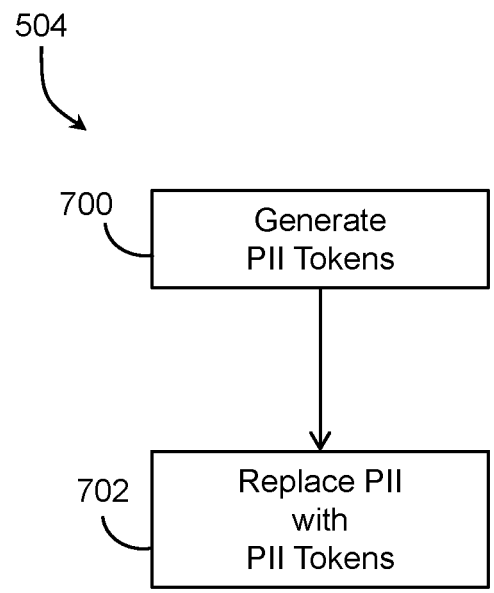
FIG. 7 is an illustrative flow diagram depicting a process performed to tokenize other data.

FIG. 7 depicts exemplary steps in performing tokenizing the other data (Step 504). First, one or more personal identification information tokens are generated from the personal identification information (PII) associated with the other data (Step 700). Then the personal identification information (PII) associated with the other data is replaced with the generated personal identification information token (Step 702). The generation of personal identification information tokens is performed by tokenizing or otherwise encrypting the personal identification information (PII) using a unique encryption key. In the embodiment of FIG. 4, the second instance of the de-identifying software 404 is downloaded to the second client site 402 from the central management platform 104. In some embodiments, the de-identifying software 404 is part of other software operating on the second client site. In some embodiments, the de-identifying software 404 includes a unique encryption key, sometimes called a salt, as well as the necessary configuration for generating the tokens. In other embodiments, the de-identifying software 404 contacts the central management platform 104 to obtain the unique encryption key and configurations. The encryption key provided is unique to the second client site and the trial. Thus, the tokens generated using the unique encryption key are unique to the second client site and the trial. In some embodiments, de-identifying the other data also includes formatting or otherwise configuring the data in addition to the tokenizing. It should also be understood that the tokenizing of the other data can be performed by or on any of the other entities. Other deployments or configurations will be apparent to one skilled in the art given the benefit of this disclosure.

Figure 8:
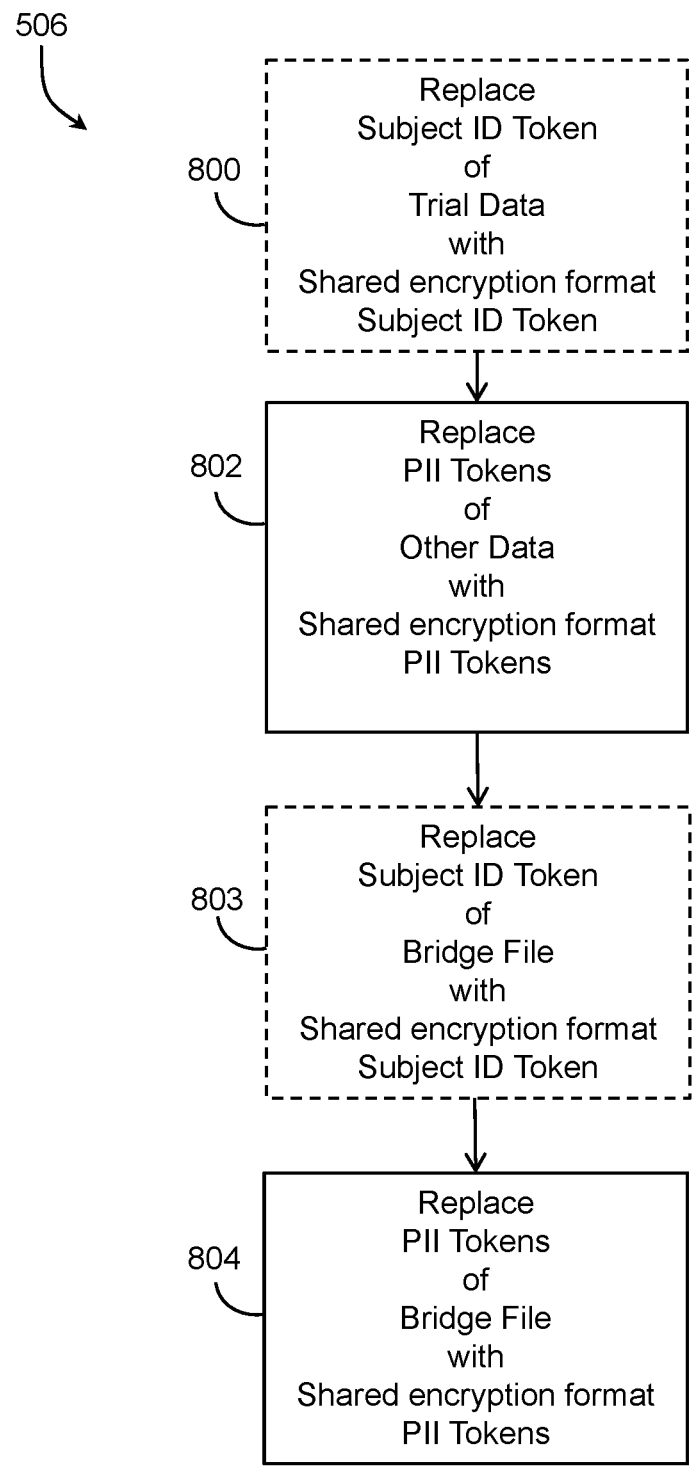
FIG. 8 is an illustrative flow diagram depicting a process performed to link trial data to tokenized other data.

FIG. 8 depicts exemplary steps in performing linking the trial data for the subject to the tokenized other data for the subject (Step 506). If the subject ID is of the trial data is tokenized, the subject identification token associated with the trial data is replaced with a shared encryption format subject identification token (Step 800). If the subject identification of the trial data is not tokenized, this step (step 800) can be skipped. The one or more identification information tokens associated with the other data are replaced with one or more shared encryption format personal identification information tokens (Step 802). If the subject identification of the trial data is tokenized, the subject ID token in the bridge file is also replaced with shared encryption format Subject ID token (Step 803). If the trial data is not tokenized, this step can also be skipped. The one or more identification information tokens in the bridge file are also replaced with the one or more shared encryption format personal identification information tokens (Step 804). Replacing of tokens is performed by decrypting the tokens and then re-encrypting them into the shared encryption format. The data with shared encryption format tokens 422 is now linked. In the embodiment of FIG. 4, the linking software 406 is downloaded to the trial originator or sponsor 106 from the central management platform 104. In some embodiments, the linking software 406 is part of other software operating on the trial originator or sponsor 106. In some embodiments, the linking software 406 includes a unique encryption key, sometimes called a salt, as well as the necessary configuration for generating the replacement tokens. In other embodiments, the linking software 406 contacts the central management platform 104 to obtain the unique encryption key and configurations. The encryption key provided is unique to the trial originator or sponsor 106 and the trial. Thus, the tokens generated using the unique encryption key are unique to the trial originator or sponsor 106 and the trial. In some embodiments, de-identifying the trial data also includes formatting or otherwise configuring the data. It should also be understood that the de-identifying of the trial data can be performed by or on any of the other entities. Other deployments or configurations will be apparent to one skilled in the art given the benefit of this disclosure.

Figure 9:
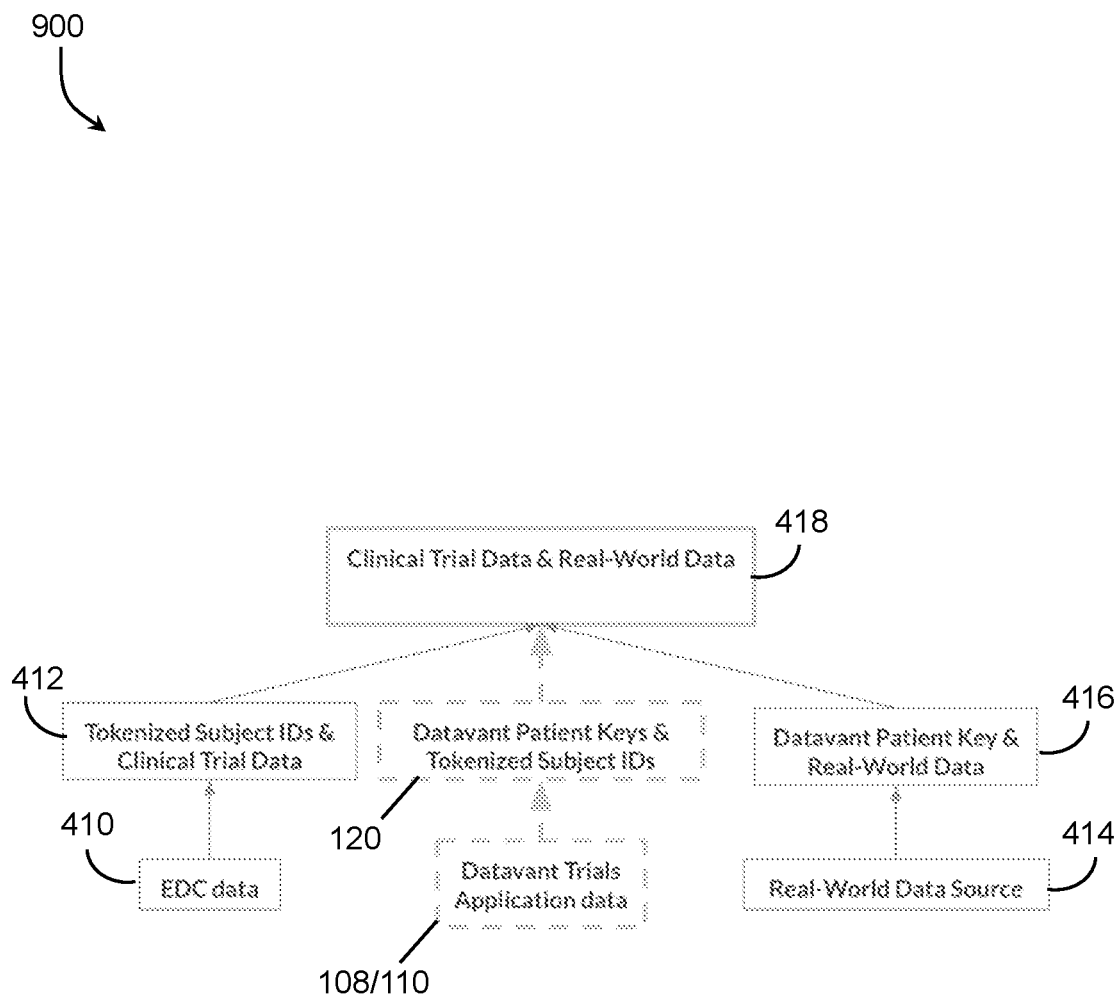
FIG. 9 is diagrammatic illustration depicting the linking of trial data to tokenized other data.

FIG. 9 depicts the linking or merging of data 900 using the systems and methods of the present invention in accordance with one embodiment. Personal identification information (PII) 108 and subject identification (subject ID) 110 are used to generate a bridge file 120 having the subject identification (Subject ID) (or in this case, subject identification token) linked to multiple personal identification tokens. Trial data 410 can optionally be tokenized to trial data with subject identification tokens. Other data 414 is tokenized to other data with one or more personal identification tokens 416. The trial data 410 or optionally the tokenized trial data 412 is then linked to the other tokenized data 416 using the bridge file 120 resulting in linked but still de-identified data including both the trial and other data 418.

Figure 10:
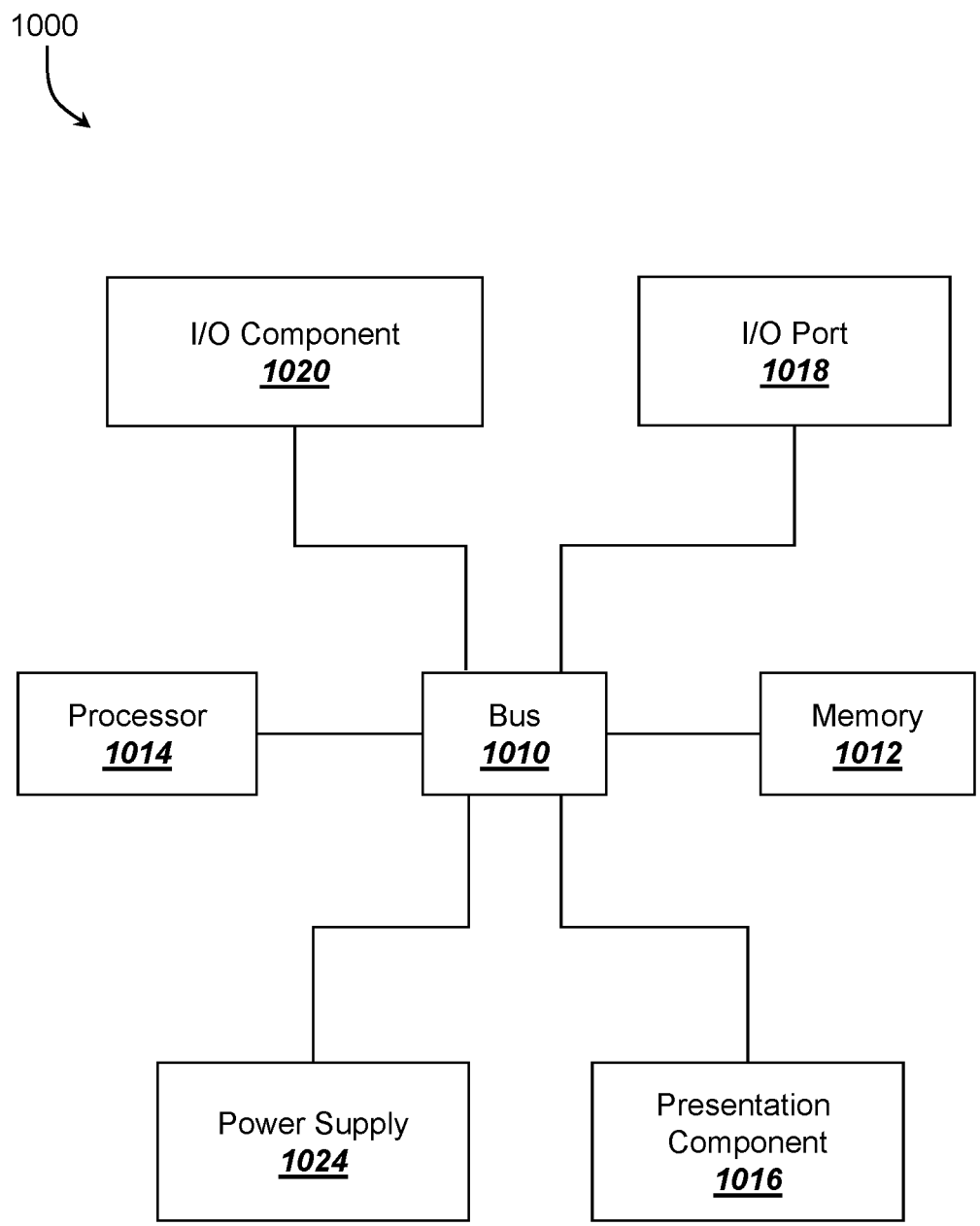
FIG. 10 is a diagrammatic illustration of a high-level architecture for devices implementing processes.

Any suitable computing device can be used to implement the entities 102, 104, 106, 414 and methods/functionality described herein. One illustrative example of such a computing device 1000 is depicted in FIG. 10. The computing device 1000 is merely an illustrative example of a suitable computing environment and in no way limits the scope of the present invention. A "computing device," as represented by FIG. 10, can include a "workstation," a "server," a "laptop," a "desktop," a "hand-held device," a "mobile device," a "tablet computer," or other computing devices, as would be understood by those of skill in the art. Given that the computing device 1000 is depicted for illustrative purposes, embodiments of the present invention may utilize any number of computing devices 1000 in any number of different ways to implement a single embodiment of the present invention. Accordingly, embodiments of the present invention are not limited to a single computing device 1000, as would be appreciated by one with skill in the art, nor are they limited to a single type of implementation or configuration of the example computing device 1000.

The computing device 1000 can include a bus 1010 that can be coupled to one or more of the following illustrative components, directly or indirectly: a memory 1012, one or more processors 1014, one or more presentation components 1016, input/output ports 1018, input/output components 1020, and a power supply 1024. One of skill in the art will appreciate that the bus 1010 can include one or more busses, such as an address bus, a data bus, or any combination thereof. One of skill in the art additionally will appreciate that, depending on the intended applications and uses of a particular embodiment, multiple of these components can be implemented by a single device. Similarly, in some instances, a single component can be implemented by multiple devices. As such, FIG. 10 is merely illustrative of an exemplary computing device that can be used to implement one or more embodiments of the present invention, and in no way limits the invention.

The computing device 1000 can include or interact with a variety of computer-readable media. For example, computer-readable media can include Random Access Memory (RAM); Read Only Memory (ROM); Electronically Erasable Programmable Read Only Memory (EEPROM); flash memory or other memory technologies; CDROM, digital versatile disks (DVD) or other optical or holographic media; magnetic cassettes, magnetic tape, magnetic disk storage or other magnetic storage devices that can be used to encode information and can be accessed by the computing device 1000.

The memory 1012 can include computer-storage media in the form of volatile and/or nonvolatile memory. The memory 1012 may be removable, non-removable, or any combination thereof. Exemplary hardware devices are devices such as hard drives, solid-state memory, optical-disc drives, and the like. The computing device 1000 can include one or more processors that read data from components such as the memory 1012, the various I/O components 1016, etc. Presentation component(s) 1016 present data indications to a user or other device. Exemplary presentation components include a display device, speaker, printing component, vibrating component, etc.

The I/O ports 1018 can enable the computing device 1000 to be logically coupled to other devices, such as I/O components 620. Some of the I/O components 1020 can be built into the computing device 1000. Examples of such I/O components 1020 include a microphone, joystick, recording device, game pad, satellite dish, scanner, printer, wireless device, networking device, and the like.

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about", "generally", and "approximately" are intended to cover variations that may existing in the upper and lower limits of the ranges of subjective or objective values, such as variations in properties, parameters, sizes, and dimensions. In one non-limiting example, the terms "about", "generally", and "approximately" mean at, or plus 10 percent or less, or minus 10 percent or less. In one non-limiting example, the terms "about", "generally", and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A method of linking trial data for a subject with other tokenized data for the subject, the method comprising:
   receiving, by trial token generation software at a first client site, an identification of the subject in the trial (subject ID);
   receiving, by the trial token generation software at the first client site, personal identification information (PII) for the subject;
   generating, using the trial token generation software at the first client site, multiple tokens from the personal identification information (PII) for the subject, wherein the multiple personal identification information tokens are unique to the first client site and the subject;
   generating, using the trial token generation software at the first client site, a bridge file mapping a link between the identification of the subject in the trial (subject ID) and the multiple personal identification information tokens; and
   sending, using the trial token generation software, the bridge file from the first client site to a storage location;
   wherein the bridge file links trial data for the subject identified by the identification of the subject in the trial (subject ID) to other data for the subject tokenized with the multiple personal identification information tokens; and
   wherein, only the first client site has access to the identification of the subject in the trial (subject ID), personal identification information (PII), and the link between the identification of the subject in the trial (subject ID) and personal identification information for the subject.

2. The method of claim 1 wherein the trial token generation software is downloaded from a central management platform (vault).

3. The method of claim 1, further comprising registering, by a trial originator/sponsor, the trial with a central management platform (vault).

4. The method of claim 1, further comprising registering the first client site with a central management platform and wherein the central management platform assigns a unique encryption key to the first client site, the unique encryption key used by the trial token generation software to generate the multiple personal identification information tokens.

5. The method of claim 1, wherein multiple subjects participate in the trial and an identification of the subject in the trial (subject ID) and personal identification information (PII) for each of the multiple participants is provided and multiple personal identification tokens are generated for each of the multiple participants in the trial, and wherein the bridge file links the identification of the subject in the trial (subject ID) and multiple personal identification tokens for each participant in the trial.

6. The method of claim 1, wherein the storage location is located at a trial originator/sponsor.

7. The method of claim 1, further comprising:
   assigning, at the first client site, an identification for a subject (subject ID) in the trial; and
   collecting, at the first client site, personal identification information (PII) for the subject in the trial.

8. The method of claim 1, further comprising:
   obtaining, at the first client site, the subject's consent for participation in the trial.

9. The method of claim 1, wherein generating a-multiple personal identification tokens and generating a bridge file, are performed as a batch process where the personal identification information is sent to a secure location where an application at the secure location generates the multiple personal identification tokens and returns the personal identification tokens to the trial token generation software.

10. The method of claim 1, further comprising:
    tokenizing, with de-identification software, other data for the subject using one or more personal identification information tokens; and
    linking, with linking software, the trial data for the subject to the tokenized other data for the subject using the bridge file.

11. The method of claim 10, wherein tokenizing, with de-identification software, other data is performed at a second client site.

12. The method of claim 11, further comprising registering the second client with central management platform (vault) and wherein the central management platform assigns a unique encryption key to the second client site, the unique encryption key used by the de-identification software to generate the one or more personal identification information tokens.

13. The method of claim 12, wherein the de-identification software is downloaded from a central management platform (vault).

14. The method of claim 10, wherein tokenizing other data for the subject comprises:
- generating one or more personal identification information tokens from the personal identification information of the subject; and
- replacing the personal identification information (PII) associated with the subject with one or more personal identification information tokens.

15. The method of claim 10, wherein the linking software is downloaded from a central management platform (vault).

16. The method of claim 10, wherein linking the trial data for the subject to the tokenized other data for the subject is performed at a trial originator/sponsor.

17. The method of claim 10, wherein linking the trial data for the subject to the tokenized other data for the subject comprises:
- replacing the one or more identification information tokens associated with the other data with one or more shared encryption format person identification information tokens;
- replacing the one or more personal identification information tokens in the bridge file with one or more shared encryption format personal identification information tokens; and
- linking the trial data of the subject to the other data for the subject based on the shared encryption format tokens.

18. The method of claim 1, further comprising:
- generating, using trial token generation software at a first client site, a subject identification token from an identification of subject in the trial (subject ID), wherein the subject identification token is unique to the first client site and the trial;
- wherein the generated bridge file maps a link between the subject identification token and the multiple personal identification information tokens; and
- wherein the bridge file links trial data for the subject tokenized with the subject identification token to other data for the subject tokenized with the multiple personal identification information tokens.

19. The method of claim 18, further comprising registering the first client site with a central management platform and wherein the central management platform assigns a unique encryption key to the first client site, the unique encryption key used by the trial token generation software to generate the subject identification token and the multiple personal identification information tokens.

20. The method of claim 18, wherein multiple subjects participate in the trial and a subject identification token and multiple personal identification tokens are generated for each of the multiple participants in the trial, and wherein the bridge file links the subject identification token and multiple personal identification tokens for each participant in the trial.

21. The method of claim 18, wherein generating a subject identification token, generating a-multiple personal identification tokens, and generating a bridge file, are performed as a batch process where the subject identification and personal identification information is sent to a secure location where an application at the secure location generates the subject identification token and the multiple personal identification token and returns the subject identification token and the personal identification token to the trial token generation software.

22. The method of claim 18, further comprising:
- tokenizing, with de-identification software, trial data using a subject identification token;
- tokenizing, with de-identification software, other data for the subject using one or more personal identification information tokens; and
- linking, with linking software, the tokenized trial data for the subject to the tokenized other data for the subject using the bridge file.

23. The method of claim 22, wherein tokenizing trial data comprises:
- generating a subject identification token from the identification of the subject in the trial (subject ID); and
- replacing the identification of the subject (subject ID) associated with the trial data with a subject identification token.

24. The method of claim 22, wherein tokenizing trial data, with de-identification software, is performed at the trial originator/sponsor.

25. The method of claim 24, further comprising registering the trial originator/sponsor with central management platform (vault) and wherein the central management platform assigns a unique encryption key to the trial originator/sponsor, the unique encryption key used by the de-identification software to generate the subject identification token.

26. The method of claim 25, wherein the de-identification software is downloaded from a central management platform (vault).

27. The method of claim 22, wherein tokenizing other data for the subject comprises:
- generating one or more personal identification information tokens from the personal identification information of the subject; and
- replacing the personal identification information (PII) associated with the trial data with one or more personal identification information tokens.

28. The method of claim 22, wherein linking the tokenized trial data for the subject to the tokenized other data for the subject is performed at a trial originator/sponsor.

29. The method of claim 22, wherein linking the tokenized trial data for the subject to the tokenized other data for the subject comprises:
- replacing the subject identification token associated with the trial data with a shared encryption format subject identification token;
- replacing the one or more identification information tokens associated with the other data with one or more share encryption format personal identification information tokens;
- replacing the subject identification token linked to the one or more personal identification information tokens in the bridge file with a shared encryption format subject identification token linked to one or more shared encryption format personal identification information tokens; and
- linking the trial data of the subject to the other data for the subject based on the shared encryption format tokens.

30. A method of linking tokenized trial data for a subject with other tokenized data for the subject, the method comprising:
- generating, using trial token generation software at a first client site, a subject identification token from an identification of subject in the trial (subject ID), wherein the subject identification token is unique to the first client site and the trial;
- generating, using the trial token generation software at the first client site, multiple tokens from personal identification information (PII) for the subject, wherein the multiple personal identification information tokens are unique to the first client site and the subject;

generating, using the trial token generation software at the first client site, a bridge file mapping a link between the subject identification token and the multiple personal identification information tokens; and sending, using the trial token generation software, the bridge file from the first client site to a storage location;

wherein the bridge file links trial data for the subject tokenized with the subject identification token to other data for the subject tokenized with the multiple personal identification information tokens; and wherein, only the first client site has access to the subject identification (subject ID), personal identification information (PII), and the link between the subject identification and personal identification information for the subject.

* * * * *

UNITED STATES PATENT AND TRADEMARK OFFICE
CERTIFICATE OF CORRECTION

PATENT NO. : 11,550,956 B1
APPLICATION NO. : 17/464246
DATED : January 10, 2023
INVENTOR(S) : Serena Gupta et al.

It is certified that error appears in the above-identified patent and that said Letters Patent is hereby corrected as shown below:

In the Claims

Column 14, Claim 9, Line 41, delete "a-multiple" and insert --multiple--.

Signed and Sealed this
Twenty-eighth Day of March, 2023

Katherine Kelly Vidal
*Director of the United States Patent and Trademark Office*